US00PP23546P2

(12) United States Plant Patent
Kordes

(10) Patent No.: US PP23,546 P2
(45) Date of Patent: Apr. 23, 2013

(54) SHRUB ROSE PLANT NAMED 'KORBUTTE'

(50) Latin Name: *Rosa hybrida*
Varietal Denomination: KORbutte

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 13/136,223

(22) Filed: Jul. 25, 2011

(51) Int. Cl.
*A01H 5/00* (2006.01)

(52) U.S. Cl. ..... Plt./102

(58) Field of Classification Search ..... Plt./102, Plt./107
See application file for complete search history.

*Primary Examiner* — Kent L Bell

(57) ABSTRACT

A new and distinct variety of rose with long lasting, novel decorative orange-red hips, and attractive foliage with excellent disease resistance. It exhibits uniform growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORbutte'.

CROSS REFERENCES AND FEDERAL R&D STATEMENT

There are no cross referenced or related applications. This variety was developed without the aid of any research grant.

The new variety of rose plant of the present invention originated from a controlled crossing in a breeding program of two distinct parents during the summer of 2002. The crossing was between a non-patented 'un-named seedling' and a non-patented 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORbutte'.

SUMMARY OF THE INVENTION

The new rose plant may be distinguished from its seed parent, an 'un-named seedling', by the following combination of characteristics:

1. The hips of 'KORbutte' are hard while the hips of the seed parent are soft.
2. 'KORbutte' has an abundance of thorns while the seed parent only has a few.

The new rose plant may be distinguished from its pollen parent, an 'un-named seedling' by the following combination of characteristics:

1. 'KORbutte' has 30-60 hips per cluster while the pollen parent has single hips.
2. The petal count of 'KORbutte' is 14-18 (semi-double) while the petal count of the pollen parent is 26-40 (double).

The objective of the hybridization was to create a new and distinct rose plant with unique qualities, such as:

1. Uniform growth and flowering;
2. Abundant attractive hips;
3. Attractive and abundant foliage; and
3. Resistance to diseases encountered in commercial growing conditions.

This combination of qualities is not present in prior rose cultivars known to the inventor. These objectives have been substantially achieved and in that distinguish 'KORbutte' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORbutte' was selected in 2003 from the seedling beds to be asexually propagated for further evaluation. The first asexual propagation of 'KORbutte' was done by budding to seedling understocks in July, 2003 at the inventor's nursery in Offenseth-Sparrieshoop, Germany.

This initial and other subsequent propagations conducted in controlled environments demonstrate that 'KORbutte' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORbutte'.

DETAILED BOTANICAL DESCRIPTION

The following is a description of 'KORbutte', as observed growing in October, 2010 and July, 2011 in a nursery in Jackson County, Oreg. on plants of 3 years of age. Color references are made using The Royal Horticultural Society (London, England) Colour Chart, 2001 except where common terms of color are used.

For a comparison, several physical characteristics of the rose variety 'KORcastrav', a rose variety from the same inventor described and illustrated in U.S. Plant Pat. No. 23,091, issued on Oct. 2, 2012, are compared to 'KORbutte' in Chart 1.

CHART 1

| Characteristic | 'KORbutte' | 'KORcastrav' |
|---|---|---|
| Flower bud size upon opening, on average: | 25-30 mm (l) × 15 mm (w). | 35 mm (l) × 25 mm (w). |
| General Tonality on open flower: | Red-Purple Group 60C. | Red Group 45A. |
| Average length of stipules: | 18 mm. | 25 mm. |

Parents:

*Seed parent*.—An 'un-named seedling'.

*Pollen parent*.—An 'un-named seedling'.

Classification:

*Botanical classification*.—*Rosa hybrida* 'KORbutte'.

*Commercial classification*.—Shrub rose.

FLOWER AND FLOWER BUD

Blooming habit: Recurrent.

Flower bud:

*Size*.—Upon opening, 25-30 mm in length from base of receptacle to end of bud and 15 mm diameter at its widest point.

*Bud form*.—Short. Pointed ovoid.

*Bud color*.—As sepals first unfold, bud color is Greyed-Purple Group 185A. When ¼ open, the upper surface of petals is Red Group 46A, and the lower surface is Red-Purple Group 59B. Guard Petals are Red Group 46A.

*Sepals*.—Color: Upper surface: Green Group 138B. Lower surface: Green Group 144A. Intonations of Greyed-Red Group 181 B on upper and lower sides. Size: Average 30-35 mm (l)×7 mm (w). Shape: Triangular. Sepals generally subulate. Sepal apex is generally cirrose. Foliaceous appendages on three of the five sepals. Apex: Apiculate. Base: Flat at union with receptacle. Quantity: Five. Surface texture: Upper side: dense pubescence. Lower surface: slight pubescence. Margins: Stipitate glands present.

Receptacle:

*Surface*.—Moderately pubescent.

*Color*.—Yellow-Green Group 144A, with anthocyanin color of Greyed-Red Group 183D.

*Shape*.—Funnel shaped.

*Size*.—8 mm (h)×8 mm (w).

Peduncle:

*Surface*.—With stipitate glands.

*Length*.—30 to 40 mm average length.

*Diameter*.—1.5 to 2 mm average diameter.

*Color*.—Yellow-Green Group 146C.

*Strength*.—Moderately strong.

*Borne*.—Multiple flower buds per stem, generally 15-25.

*Anthocyanin present*.—Greyed-Red Group 182A.

Flower bloom:

*Fragrance*.—None.

*Duration*.—On the plant 4 to 6 days. As a cut flower, 3 to 4 days. Senesced petals drop away cleanly.

*Size*.—Medium sized for a floribunda rose. When open, the average flower diameter is 45 mm and the average flower height is 40 mm.

*Form*.—Shape of flower when viewed from the side: Upon opening, upper part: Flattened convex. Upon opening, lower part: Convex. Open flower, upper part: Flat. Open flower, lower part: Convex.

Color:

*Upon opening, petals*.—Outermost petals: Outer Side: Red-Purple Group 60B. Inner Side: Red-Purple Group 60A. Innermost petals: Outer Side: Red-Purple Group 60C. Inner Side: Red Group 53C.

*Upon opening, basal petal spots*.—Basal petal spot, outermost petals: Outer Side: Yellow Group 1B. Inner Side: Yellow Group 1C. Basal petal spot, innermost petals: Outer Side: Yellow Group 1C. Inner Side: Yellow Group 1D.

*After opening, petals*.—Outermost petals: Outer Side: Red-Purple Group 60B. Inner Side: Red-Purple Group 60A. Innermost petals: Outer Side: Red-Purple Group 60C. Inner Side: Red Group 53C.

*After opening, basal petal spots*.—Basal petal spot, outermost petals: Outer Side: Yellow Group 1C. Inner Side: Yellow Group 1D. Basal petal spot, innermost petals: Outer Side: Yellow Group 1C. Inner Side: Yellow Group 1D.

General tonality: On open flower Red-Purple Group 60C. No change in the general tonality at the end of the 3$^{rd}$ day. Afterwards, general tonality is Red-Purple Group 57A and Red-Purple Group 65C.

Petals:

*Petal count*.—Semi-double. Approximately 14-18 petals under normal conditions.

*Petal reflex*.—Petals reflex slightly.

*Petal edge*.—Entire.

*Petal shape*.—Obovate. Apex shape is round. Shape of base is obtuse.

*Petal size*.—35 mm (l)×27 mm (w).

*Thickness*.—Thin.

*Petal arrangement*.—Not Formal.

Petaloids: Usually a few present.

*Petaloid count*.—Average of 3-5 per flower.

*Petaloid size*.—Petaloids are 12 mm (l) and 7 mm (w).

*Petaloid color*.—Color of inner side is Red Group 53B. Color of outer side is Red-Purple Group 60C.

*Petaloid texture*.—Satiny.

*Margins*.—Variable. Entire to repand.

*Petaloid shape*.—Overall: Ovate. Apex: Obtuse. Base: Pointed.

Reproductive organs:

*Pistils*.—Approximately 50 present. Stigmas: Location: Slightly superior in position to anthers. Color: Greyed-Yellow Group 160C. Styles: Length: 8-10 mm long. Color: Yellow Group 1D.

*Stamens*.—Approximately 130 on average and regularly arranged. Anthers: Size: 2 mm long, on average. Pollen: Generally present. Color: Greyed-Orange Group 163B. Filaments: Color: Yellow Group 1C. Length: 6-8 mm.

THE PLANT

*Growth*.—Vigorous

*Plant habit*.—Upright to bushy habit. When grown as a budded field grown plant, the average plant height is 100 cm and the average plant width is 70 cm.

*Stems*.—Stem color: Young wood: Greyed-Red Group 178A. Older wood: Yellow-Green Group 146B. Stem surface: Juvenile stems: Smooth. Mature stems: Smooth.

*Prickles*.—Present. Incidence: Juvenile stems: 15-20 fine prickles per 10 cm of stem. Mature stems: 15 per 10 cm of stem. Size: Juvenile stems: Average length: 5-8 mm. Mature stems: Average length: 12-15 mm. Color: Immature prickles: Greyed-Purple Group 183A. Mature prickles: Greyed-Red Group 178B. Senescing to Greyed-Orange Group 165B. Shape: Concave. Anthocyanin: Juvenile prickles: Greyed-Purple Group 183A. Mature prickles: Color Greyed-Red Group 178B.

*Leaves and leaflets*.—Normally 7 leaflets on normal leaves in middle of the stem. Venation pattern: Pyramidal net pattern. Leaf size: 115 mm (l)×80 mm (w). Abundance: Abundant. Texture: Leathery. Upper side of leaflet: Semi-glossy. Smooth. Under side of leaflet: Matte. Thin. Color, mature foliage: Upper Leaf Surface: Green Group 136A. Lower Leaf Surface: Green Group N138B. Color, juvenile foliage: Upper Leaf Surface: Yellow-Green Group 147A. Lower Leaf Surface: Green Group N138B. Anthocyanin: Present. Intonations of Greyed-Purple Group 183A present on juvenile leaf margins, veins, and undersides.

*Stipules*.—Size: 18 mm (l)×6 mm (w). Stipule color: Green Group 138A. Anthocyanin: Upper side: Greyed-Red Group 182A. Margins: Very ciliated with stipitate glands. Shape: Apex: Apiculate. Base: Winged.

*Petiole*.—Length: About 25 mm. Diameter: About 2 mm. Petiole color: Yellow-Green Group 144A on under side. Intonations of Greyed-Purple Group 183B on upper side. Underneath: Smooth. Margins: Entire. With stipitate glands. Prickles: Lacking.

*Petiole rachis*.—Length: 55 mm, on average. Diameter: 1.5 to 2 mm, on average. Color: Yellow-Green Group 144A. Underneath: Mostly smooth with 2-6 prickles per leaf. Margins: Entire, with stipitate glands. Anthocyanin: Present on top side. Greyed-Purple Group 183B.

*Leaflets*.—Size: Average size of the terminal leaflet is 45 mm (l)×25-30 mm (w). Shape: Entire leaflet: Ovate. Base: Ovate. Apex: Acute. Margins: Finely serrated. Surface: Upper: Semi-glossy. Lower: Matte. Texture: Smooth.

Hips/seed formation: Orange-Red Group 34A and 34B. Average size of hips is 10 mm (l)×10 mm (w).

Winter hardiness: To date, the variety has been grown successfully in USDA Zones 5-9.

Disease resistance: Excellent resistance to powdery mildew (*Sphaerotheca pannosa*), blackspot (*Diplocarpon rosae*), rust (*Phragmidium* sp.), and Botrytis (*Botrytis cinerea*) diseases under normal growing conditions.

Other comments: This cultivar sets durable hips on long stems suitable for floral decorative use.

I claim:

1. A new and distinct variety of rose plant, as described and illustrated herein.

* * * * *

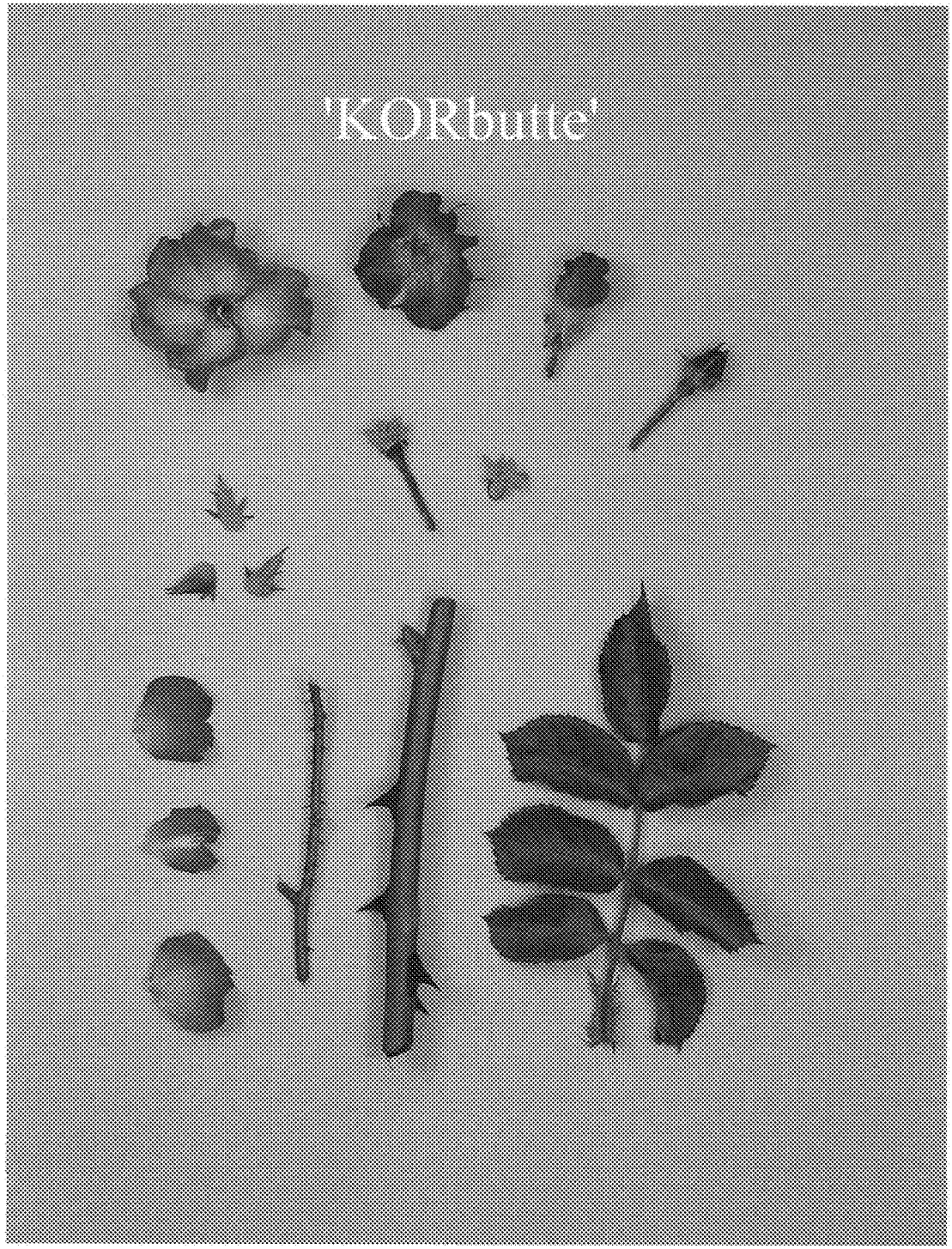
'KORbutte'